United States Patent [19]

Jenck

[11] Patent Number: 5,041,642
[45] Date of Patent: * Aug. 20, 1991

[54] PREPARATION OF BETA, GAMMA-UNSATURATED CARBOXYLIC ACIDS

[75] Inventor: Jean Jenck, Villeurbanne, France

[73] Assignee: Rhone-Poulenc Chimie de Base, Courbevoie, France

[*] Notice: The portion of the term of this patent subsequent to Feb. 21, 2001 has been disclaimed.

[21] Appl. No.: 814,807

[22] Filed: Dec. 30, 1985

Related U.S. Application Data

[63] Continuation of Ser. No. 511,922, Jul. 8, 1983, abandoned.

[30] Foreign Application Priority Data

Jul. 9, 1982 [FR] France .................. 82 12231

[51] Int. Cl.$^5$ .................. C07C 51/14; C07C 57/03
[52] U.S. Cl. .................. 562/522; 260/413; 562/406; 562/497
[58] Field of Search .................. 562/522, 406, 497; 260/413

[56] References Cited

U.S. PATENT DOCUMENTS 4,433,164 2/1984 Jenck .................. 560/207

Primary Examiner—Vivian Garner
Attorney, Agent, or Firm—Burns, Doane, Swecker & Mathis

[57] ABSTRACT

$\beta,\gamma$-Unsaturated carboxylic acids are facilely prepared by carbonylating a conjugated diene with carbon monoxide in the presence of (i) water, (ii) a halogenated hydracid, (iii) a palladium catalyst comprising palladium metal or supported palladium metal, a palladium oxide, or a complex salt of palladium, the anion coordinated to the palladium cation of which comprising a hard or borderline base, and (iv) a quaternary onium salt of nitrogen, phosphorus or arsenic, said N, P or As being tetra-coordinated to a carbon atom, the anion of which comprising a hard or borderline base.

24 Claims, No Drawings

PREPARATION OF BETA, GAMMA-UNSATURATED CARBOXYLIC ACIDS

This application is a continuation of application Ser. No. 511,922, filed July 8, 1983, now abandoned.

BACKGROUND OF THE INVENTION

1. Field of the Invention

The present invention relates to the preparation of $\beta,\gamma$-unsaturated carboxylic acids by reacting conjugated dienes and carbon monoxide in the presence of water.

2. Description of the Prior Art

It is known to this art, from French Patent No. 1,406,194, that 3-pentenoic acid can be prepared by reacting butadiene, carbon monoxide and water in the presence of bis-triphenylphosphine-palladium dichloride and hydrochloric acid at a temperature on the order of 120° to 140° C., under a pressure on the order of 700 bar.

However, in spite of the high pressures used, this process is of low efficiency and its selectivity as regards the desired acid is unsatisfactory.

It too is known, from French Patent No. 1,476,301, that 3-pentenoic acid can be prepared by reacting butadiene, carbon monoxide and water in the presence of palladium, hydrochloric acid and oxygen at a temperature of 100° C., under a pressure on the order of 700 bar. Although an appreciable amount of 3-pentenoic acid is obtained under these conditions, this particular method is unsatisfactory, especially because it entails use of a dangerous mixture of carbon monoxide and oxygen and the increase in the risk of corrosion connected with the simultaneous presence of water, hydrochloric acid and an oxidant in the reaction mixture. Furthermore, in spite of the high pressures used, this process remains of low efficiency and its selectivity as regards the desired acid is unsatisfactory The above reaction (carbonylation of conjugated dienes in the presence of water) is also described in U.S. Pat. No. 3,509,209. This reaction is carried out in the presence of palladium and hydrochloric acid and, if appropriate, iron compounds. However, this technique is not satisfactory because, in particular, of the low level of conversion found for the diene and its low selectivity as regards the desired acid.

It has, moreover, also been found that if the reaction of butadiene, carbon monoxide and water is carried out in the presence of palladium-II chloride and hydrochloric acid, the complex catalyst is unstable and deteriorates into granules of inactive palladium metal.

SUMMARY OF THE INVENTION

Accordingly, a major object of the present invention is the provision of an improved process for the preparation of $\beta,\gamma$-unsaturated carboxylic acids by carbonylation of conjugated dienes in the presence of water, which improved process is conspicuously devoid of those disadvantages and drawbacks to date characterizing the state of this art, and according to which the carbonylation of the conjugated dienes into the desired acids is carried out effectively and selectively under relatively mild conditions of temperature and pressure, the complex catalyst employed being moreover of satisfactory stability.

Briefly, the present invention features a novel process for the preparation of $\beta,\gamma$-unsaturated carboxylic acids by carbonylation of a conjugated diene in the presence of water, a halogenated hydracid and a palladium catalyst at a temperature greater than 60° C. and under an overall pressure (at the reaction temperature) greater than 50 bar, which novel process is characterized in that (i) the carbonylation operation is also carried out in the presence of a quaternary onium salt of an element of Group VB of the Periodic Table selected from among nitrogen, phosphorus and arsenic, this element being tetra-coordinated to the carbon atom and the salt having an anion selected from among the "hard" or "borderline" bases, and (ii) the palladium catalyst comprises palladium metal, if appropriate deposited onto suitable support, a palladium oxide or a salt or complex of palladium in which the anion coordinated to the palladium cation is a "hard" or "borderline" base.

By the terms "hard" or "borderline" base as utilized herein, there are intended any anion corresponding to the classical definition given by R. Pearson, in *J. Chem. Ed.*, 45, 581-7 (1968), i.e., the terms "hard" and "borderline" have the meanings given in this reference.

And by the expression "a quaternary onium cation in which the element of Group VB is tetra-coordinated to the carbon atom", there is intended the cations formed from nitrogen, phosphorus or arsenic and four monovalent, identical or different hydrocarbon groups, the free valency of which being borne by a carbon atom and each group being bonded to the above element via this free valency; it furthermore being possible for any two groups of this type to together form a single divalent radical.

DETAILED DESCRIPTION OF THE INVENTION

More particularly according to this invention, in a preferred embodiment thereof, the quaternary onium salt comprises a quaternary onium cation having one of the following general formulae (I) to (III):

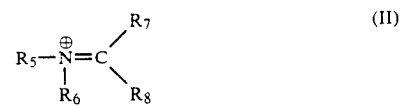

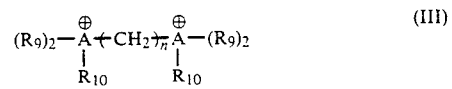

in which A represents a nitrogen, phosphorus or arsenic atom, $R_1$, $R_2$, $R_3$ and $R_4$ are identical or different and represent a straight-chain or branched alkyl radical containing 1 to 16 carbon atoms and optionally substituted by a phenyl, hydroxyl, halogen, nitro, alkoxy or alkoxy-carbonyl group, the alkoxy group comprising at most 4 carbon atoms; a straight-chain or branched alkenyl radical containing 2 to 12 carbon atoms, preferably 4 to 8 carbon atoms, and especially an alkenyl radical derived from the starting material conjugated diene; or an aryl radical containing 6 to 10 carbon atoms and optionally substituted by one or more alkyl radicals containing 1 to 4 carbon atoms, alkoxy or alkoxycarbonyl, the alkoxy group comprising at most 4 carbon atoms, or halogen; or two of such radicals $R_1$ to $R_4$ can together form a straight-chain or branched alkylene, alkenylene or alkadienylene radical containing 3 to 6 carbon atoms; $R_5$, $R_6$, $R_7$ and $R_8$ are identical or different and represent a straight-chain or branched alkyl radical containing 1 to 4 carbon atoms; or the radicals $R_7$ and $R_8$ can together form an alkylene radical containing 3 to 6 carbon atoms; or the radicals $R_6$ and $R_7$, or $R_6$ and $R_8$ can together form an alkylene, alkenylene or alkadienylene radical which contains 4 carbon atoms and, with the nitrogen atom, constitutes a nitrogen-containing heterocyclic radical; $R_9$ represents a straight-chain or branched alkyl radical containing 1 to 4 carbon atoms, or a phenyl radical; $R_{10}$ represents a straight-chain or branched alkyl radical which contains 1 to 4 carbon atoms and is identical to or different from $R_9$; or a straight-chain or branched alkenyl radical containing 2 to 12 carbon atoms, preferably 4 to 8 carbon atoms, especially an alkenyl radical derived from the conjugated diene to be carbonylated; and n represents an integer greater than or equal to 1 and less than or equal to 10, preferably less than or equal to 6.

Of the "hard" or "borderline" bases which can form the anion of the above onium salts, the following ions are representative: $F^-$, $ClO_4^-$, $PF_6$, $BF_4$, $B(Ph)_4^-$, $PO_4^{3-}$, $HPO_4^2$, $H_2PO_4^-$, $CH_3SO_3^-$, $Ph\text{-}SO_3^-$, $HSO_4^-$, $NO_3^-$, $SO_4^{2-}$, $Cl^-$ and $Br^-$, Ph representing a phenyl radical, and all of the other anions falling within the Pearson definition of a "hard" or "borderline" base.

Because they are convenient to use, the subject anions are advantageously selected from among $PO_4^{3-}$, $HPO_4^{2-}$, $H_2PO_4^-$, $CH_3SO_3^-$, $Ph-SO_3^-$, $NO_3^-$, $SO_4^{2-}$, $PF_6^-$, $Cl^-$ and $Br^-$, with Ph being as above-defined. The anions $Cl^-$ and $Br^-$, especially the anion $Cl^-$, are preferably used.

The following cations are exemplary of quaternary onium cations having the general formula (I): tetramethylammonium, triethylmethylammonium, tributylmethylammonium, trimethylpropylammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltriphenylammonium, but-2-enyltriethylammonium, N,N-dimethyl-tetramethyleneammonium, N,N-diethyl-tetramethyleneammonium, tetramethylphosphonium, tetrabutylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyltri(isopropyl)phosphonium, methyltri(n-propyl)phosphonium, methyl-tri(n-butyl)phosphonium, methyltri(-methyl-2propyl)phosphonium, methyltricyclohexylphosphonium, methyltriphenylphosphonium, methyltribenzylphosphonium, methyltri(methyl-4phenyl)phosphonium, methyltrixylylphosphonium, diethylmethylphenylphosphonium, dibenzylmethylphenylphosphonium, ethyltriphenylphosphonium, tetraethylphosphonium, ethyltri(n-propyl)phosphonium, triethylpentylphosphonium, hexadecyltributylphosphonium, ethyltriphenylphosphonium, n-butyltri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, and tetraphenylarsonium.

Representative cations having the general formula (II) include the following: N-methylpyridinium, N-ethylpyridinium, N-hexadecylpyridinium and N-methylpicolinium.

And exemplary cations having the general formula (III) include the following: 1,3-bis(but-2-enyldimethylammonium)-propane, 1,2-bis(trimethylammonium)-ethane, 1,3-bis(trimethylammonium)-propane, 1,4-bis trimethylammonium)-butane and 1,3-bis(trimethylammonium)-butane.

If the onium salt contains $Cl^-$ or $Br^-$ as the anion, and contains as the cation a cation of the general formulae (I) to (III) in which one of the radicals $R_1$ to $R_4$ or the radical $R_{10}$ is an alkenyl radical derived from the start material conjugated diene, it may be advantageous to prepare the onium salt "in situ" instead of preparing it prior to the carbonylation operation.

In fact, it is particularly easy to prepare this type of product by the action of a tertiary amine on, for example, the product or products of the reaction of the starting material conjugated diene and hydrochloric acid or hydrobromic acid.

Thus, if the conjugated diene to be carbonylated is 1,3-butadiene, butenyl-trialkylammonium chloride or bromide, which can be obtained "in situ" in the carbonylation medium by the action of a tertiary alkylamine on 1-chloro- or 1-bromo-but-2-ene or on 3-chloro- or 3-bromo-but-1-ene, will be used as the quaternary onium salt; if the tertiary amine is triethylamine, for example, a butenyltriethylammonium chloride or bromide will thus be prepared "in situ".

Palladium catalysts which are useful to carry out the process according to the invention include palladium metal deposited onto a support, such as charcoal, alumina, silica, and the like; palladium oxides, salts or π-allyl complexes of palladium, the anion of which being coordinated to the palladium cation is selected from the following anions: carboxylates, such as formate, acetate, propionate and benzoate; and $SO_4^{2-}$, $NO_3^-$, acetylacetonate and halides, such as $Cl^-$ and $Br^-$, preferably $Cl^-$; and palladium-O complexes which include organic ligands which do not contain elements of Group VB, namely, complexes such as bis-(dibenzalacetone)-palladium or bis-(1,5-cyclooctadiene)-palladium.

The process according to the invention is of particular interest for the preparation of β,γ-unsaturated carboxylic acids derived from conjugated dienes having the 1,3-butadiene skeleton in their molecule.

Conjugated dienes having the 1,3-butadiene skeleton in their molecule include straight-chain or branched aliphatic dienes containing 4 to 12 carbon atoms, preferably 4 to 8 carbon atoms, and optionally substituted by inert groups such as phenyl, cyclohexyl, nitro or oxo, and cyclic dienes containing 6 to 8 carbon atoms.

Specific examples of representative conjugated dienes are 1,3-butadiene, isoprene, piperylene, 1,3-hexadiene, 2,4-hexadiene, chloroprene, 1-cyclohexyl-1,3-butadiene, 1-phenyl-1,3-butadiene, 2,4-octadiene, 3-methyl-1,3-pentadiene, 2-methyl-2,4-pentadiene, 1,3-cyclohexadiene and 1,3-cyclooctadiene.

The carbonylation operation is advantageously carried out in the presence of hydrochloric acid or hydrobromic acid, especially in the presence of hydrochloric acid.

The hydrochloric acid can be introduced into the carbonylation mixture in gaseous form, in the form of an aqueous solution or in the form of an organic compound capable of liberating hydrochloric acid in the mixture, for example, in the form of 1-chloro-but-2-ene or 3-chloro-but-1-ene, in the case of carbonylation of butadiene. The method of actual introduction thereof will depend above all on practical considerations.

The amounts of reactants used to carry out the process according to the present invention can vary over very wide limits; it is obvious that these amounts will be selected in a manner such that the overall economy of the process is maximized.

Thus, although it is possible to use 0.1 to 5 times the stoichiometrically required amount of water, it is preferable, in order to avoid any risk of precipitation of palladium in the form of metallic granules (precipitation resulting from too large an amount of water), to carry out the process employing a molar ratio of water/conjugated diene ranging from about 0.5:1 to 2:1 and, advantageously, employing a molar ratio of water/conjugated diene of less than or equal to 1:1.

In the same manner, the good activity of the palladium catalysts enables a very small amount of these catalysts to be used (corresponding to a molar ratio of conjugated diene/palladium on the order of 2,500:1); the use of a larger amount of catalyst (corresponding to a molar ratio of conjugated diene/palladium on the order of 100:1) is not detrimental; since the object is to carry out a carbonylation operation sufficiently rapidly and selectively without consuming too much catalyst, a ratio of conjugated diene/palladium ranging from about 150:1 to 2,000:1, in particular ranging from about 200:1 to 1,500:1, is generally preferable. It has been found that a molar ratio ranging from about 500:1 to 700:1 generally provides good results.

It too has been found that the favorable influence provided by the presence of a quaternary onium salt corresponding to the definition given above in the carbonylation mixture is perceptible utilizing a molar ratio of onium cation/palladium of 15:1; notably, a particularly interesting effect has been found when this ratio ranges from 20:1 to 300:1, although a higher ratio is not harmful to the carbonylation reaction.

In another preferred embodiment of the subject carbonylation process, the ratio of onium cation/palladium will preferably be selected taking into consideration the concentration of palladium in the mixture, and in particular the molar ratio of conjugated diene/palladium; thus, the higher the ratio of conjugated diene/palladium, the more advantageous the use of a higher onium cation/palladium ratio.

The minimum amount of halogenated hydracid to be used depends to a large extent on the nature of the anion of the quaternary onium salt defined above.

In fact, if $Cl^-$ or $Br^-$ is selected as the anion of the quaternary onium salt, the amount of halogenated hydracid to be used corresponds to a molar ratio of halogenated hydracid/palladium of at least 5:1. However, in order to avoid any risk of precipitation of the palladium in the form of metallic granules (precipitation resulting from too low a concentration of hydracid in the mixture), or to avoid a side reaction between the hydracid and the products of the carbonylation reaction (resulting from too high a concentration of hydracid in the mixture), a molar ratio of halogenated hydracid/palladium ranging from 10:1 to 150:1, preferably ranging from 20:1 to 100:1, will advantageously be selected.

On the other hand, if the anion of the quarternary onium salt used is other than $Cl^-$ or $Br^-$, it is advantageous to use an additional amount of halogenated hydracid corresponding to the amount of quaternary onium cations thus introduced.

However, in order to simplify the description of that which follows, this additional amount is not taken into account in the molar ratio of halogenated hydracid/palladium, but it is assumed to have been added in those cases where necessary.

The elementary entities corresponding to the term "mols" are as follows:
(1) Water: gram molecule
(2) Conjugated diene: gram molecule
(3) Halogenated hydracid: gram molecule
(4) Palladium: gram atom
(5) Quaternary onium cation: gram ion The carbonylation operation will generally be carried out at a temperature ranging from 60° to 170° C., preferably from 90° to 140° C., under a carbon monoxide pressure ranging from 50 to 500 bars, preferably from 80 to 300 bars.

The temperature and pressure are selected as a function of the activity and/or the selectivity desired for a given catalyst such as to obtain the best possible results. In fact, it is known that if the temperature is reduced, the rate of conversion of the diene is reduced, but the selectivity for the desired monoacid increases. It has also been found that if the pressure of carbon monoxide is increased, the selectivity for the desired monoacid is increased.

The process according to the invention can be carried out continuously or discontinuously; it has been found that an acceptable level of conversion of 1,3-butadiene was obtained in a discontinuous operation over the course of 2 to 5 hours. If the process in question is of low sensitivity in the presence of inert gases, such as nitrogen, argon or carbon dioxide, which can be present in addition to the carbon monoxide, it will, however, be convenient to ensure that the hydrogen which tends to be present in technical grade carbon monoxide does not exceed 3 to 5% by volume, in order to restrict any hydrogenation of the conjugated diene.

In order to further illustrate the present invention and the advantages thereof, the following specific examples are given, it being understood that same are intended only as illustrative and in nowise limitative.

EXAMPLES 1 to 16

Comparative Experiments (a) and (b)

Preparation Of 3-Pentenoic Acid From Butadiene

The following conventions are used in the Examples 1 to 16 and the Tables which follow:
Ref.: reference to the particular example (or to the comparative experiment);
mmol: millimol;
BD: 1,3-butadiene;

H+: hydracid, namely, HCl used in the form of an aqueous solution for Example 6, HBr used in the form of 1-bromo-but-3-ene in Example 9, HCl used in the form of 1-chloro-but-3-ene in all other examples or comparative experiments;

Pd: palladium catalyst used in the form of bis[chloro-π-allyl-palladium-(II)] in Examples 6 and 10, bis(dibenzylacetone)palladium in Example 9, PdCl$_2$ in all the other examples and comparative experiments;

H$_2$O/BD: molar ratio of water to butadiene;

BD/Pc: molar ratio of butadiene to palladium;

H+/Pd: molar ratio of halogenated hydracid to palladium;

Additive: in principle, an onium salt, the nature of which is specified by reference to the "condensed" formulae, in which Me designates a methyl radical, Bu designates an n-butyl radical, Hex designates an n-hexyl radical, Hep designates an n-heptyl radical, Oct designates an n-octyl radical;

Additive/Pd: molar ratio of the onium salt to palladium;

T: temperature in °C.;

P(CO): pressure of the carbon monoxide in bar, the presence of the symbol = in front of the value of this pressure means that the operation is carried out under constant pressure, the absence of this symbol means that the carbonylation operation is carried out under a pressure which is not constant, (these two modes of operation are specified in the text which follows);

t: duration of the experiment at the reaction temperature, expressed in hours;

Stb: stability of the palladium, based upon the observation: of an absence of precipitation of palladium, noted by the symbol +, of a significant precipitation of palladium, noted by the symbol O;

TT: overall level of the conversion of butadiene (in %);

RT: number of mols of product, based on 100 mols of butadiene converted;

A: activity of the catalyst, expressed as the number of mols of 3-pentenoic acid obtained per mol of palladium and per hour;

P$_3$: 3-pentenoic acid;

P': 2-methyl-3-butenoic acid;

PA: pentanoic and 2-methyl-butanoic acids;

AC9: 3,8-nonadienoic acid;

DC6: diacids with 6 carbon atoms (usually 2-methyl-1,5-pentadienoic acid);

C4: butenes;

VCH: vinylcyclohexane;

tr: traces.

General mode of operation

The palladium catalyst, water, in which, where appropriate, hydrogen chloride gas had been dissolved, 1-chloro-but-3-ene or 1-bromo-but-3-ene, where appropriate, and, where appropriate, an additive were introduced, under a current of argon, into an 125 cm$^3$ autoclave of a nickel/molybdenum alloy of trade name HASTELLOY B2, which was equipped with a removable head and a valve.

The head of the autoclave was then screwed on; butadiene was subsequently introduced into the autoclave, by means of the above valve. Carbon monoxide was then introduced. This introduction was carried out in different ways, according to the operation, under constant pressure or under a pressure which was not constant.

Carbonylation under a constant pressure of CO

The autoclave, which was agitated by shaking, was brought to the temperature (T) while charging therein technical grade gaseous carbon monoxide, containing about 0.8% by volume of hydrogen, under constant pressure [P(CO)]. The reaction was allowed to proceed at this temperature for time (t).

Carbonylation under a pressure of CO which is not constant

Technical grade carbon monoxide, containing about 0.8% by volume of hydrogen, for example, 120 bar (CNT) in Example 1, was introduced and the autoclave was brought to the temperature (T). The pressure in the autoclave reached the value indicated by [P(CO)], for example, 145 bar in Example 1. The reaction was allowed to proceed at the temperature indicated for time (t), and the pressure inside the autoclave was allowed to drop little by little.

After a time (t) at the temperature indicated, under a pressure which either was or was not constant, the autoclave was cooled to 15° C. and was slowly degassed. The resulting reaction mass was esterified with the aid of acetyls in an acid medium and was then analyzed by gas chromatography. The various acids contained in the reaction mass were thus analyzed in the form of their esters.

(The reliability of the method was checked, on the one hand, by ascertaining, by potentiometry, that at least 95% of the acid groups —COOH had been esterified and, on the other hand, by subjecting samples obtained by esterification of each acid in question and of known mixtures of the various reaction products to analysis beforehand).

In addition, during degassing of the autoclave, the gas was collected in ethanol at −78° C. and the butenes (hydrogenation products of butadiene) were determined by gas chromatography.

The nature and amount of additive and the amounts of reactants and catalyst are reported in Table I which follows. The particular conditions are also reported in this table.

The results obtained are reported in Table II which follows and in which the nature of the additive used has also been given.

The control experiment (a) carried out in the absence of additive, demonstrated that, in the absence of additive, the palladium catalyst was unstable, the yield (RT) of 3-pentenoic acid was very low and the amount of butenes formed was very significant.

The control experiment (b) carried out in the presence of a mineral chloride (which is not an additive falling within the scope of the present invention) demonstrated that, in the presence of a mineral chloride, the palladium catalyst was unstable and the yield (RT) of 3-pentenoic acid was not very high (64.5%).

Example 16, carried out in the presence of an additive according to the invention, demonstrated the advantage of this type of additive, since, in the presence of such an additive, the palladium catalyst was stable and the yield (RT) of 3-pentenoic acid reached 82%.

Examples 1 to 4 illustrate the use of various quaternary onium chlorides. The palladium catalyst was stable; the yield of 3-pentenoic acid was on the order of 75 to 85%. Examples 5 to 8 illustrate the use of tetrabutylphosphonium chloride under various conditions.

Example 9 evidenced that quaternary onium bromides were less active than the corresponding chlorides, but the bromides in question also stabilized the palladium catalyst and provided a satisfactory yield of the desired acid.

Examples 10 and 13 illustrate diverse variations in the operating conditions.

Examples 14 and 15 show the advantage of using a low molar ratio of H₂O/BD.

In all of these examples, traces of various compounds which were not mentioned in Table II were detected, The molar ratios were as follows: water/isoprene equals 1.00:1; isoprene/Pd equals 657:1; HCl (originating from the chlorobutene)/Pd equals 50:1; and $Bu_4P^+Cl^-$/Pd equals 57.7:1.

After two hours of reaction at 100° C. under 145 bar (pressure not constant), the reaction mixture was analyzed as described in the preceding examples.

In particular, the reaction mixture contained the following products: 135.5 mmols of 4-methyl-3-pentenoic acid, 9.2 mmols of 2,3-dimethyl-3-butenoic acid and 29.3 mmols of hydrogenation products of the double bonds C=C of the above acids (4-methylpentanoic acid and 2,3-dimethylbutanoic acid).

TABLE I

| Ref | BD mmol | H₂O mmol | H⁺ mmol | Pd mmol | H₂O/BD | BD/Pd | H⁺/Pd | ADDITIVE nature | mmol | Additive/Pd | T | P(CO) | t |
|---|---|---|---|---|---|---|---|---|---|---|---|---|---|
| 1 | 278 | 278 | 21.2 | 0.43 | 1.00 | 657 | 50 | $Bu_4N^+Cl^-$ | 48.8 | 115 | 100 | 145 | 2 |
| 2 | " | " | " | " | " | " | " | $MeBu_3N^+Cl^-$ | " | " | " | " | " |
| 3 | 269 | " | " | " | 1.03 | 634 | " | $MeOct_3N^+Cl^-$ | " | " | " | " | " |
| 4 | 278 | " | " | " | 1.00 | 657 | " | $Hex_4N^+Cl^-$ | 24.4 | 58 | " | =145 | " |
| 5 | 250 | " | 50.0 | 1.00 | 0.90 | 250 | " | $Bu_4P^+Cl^-$ | 50.0 | 50 | 90 | 145 | " |
| 6 | 278 | " | 64.0 | 0.43 | 1.00 | 657 | 150 | " | 21.2 | 50 | 120 | 120 | " |
| 7 | " | " | 21.2 | " | " | " | 50 | " | 24.4 | 58 | 100 | =200 | " |
| 8 | " | " | " | " | " | " | " | " | " | " | " | =80 | " |
| 9 | 315 | " | " | " | 0.88 | 745 | " | $Hep_4N^+Br^-$ | 16.3 | 38 | " | 145 | " |
| 10 | 278 | " | " | " | 1.00 | 657 | " | $Bu_4N^+Cl^-$ | 48.8 | 115 | " | 145 | " |
| 11 | " | " | " | " | " | " | " | $Bu_4P^+Cl^-$ | 24.4 | 58 | 120 | =145 | " |
| 12 | " | " | " | 0.22 | " | 1264 | 100 | " | " | 115 | 100 | =145 | " |
| 13 | " | " | " | 1.27 | " | 219 | 17 | " | " | 20 | " | =145 | " |
| 14 | " | 139 | " | 0.43 | 0.50 | 657 | 50 | " | 48.8 | 115 | " | =145 | " |
| 15 | " | 555 | " | " | 2.00 | " | " | $Me_4N^+Cl^-$ | 127.3 | 300 | 120 | =145 | 5 |
| 16 | 343 | 329 | 26.7 | 0.535 | 0.96 | 641 | " | $Bu_4P^+Cl^-$ | 10.7 | 20 | 90 | =145 | 3 |
| a | 315 | 328 | " | " | 1.04 | 588 | " | — | 0 | 0 | " | =145 | " |
| b | 352 | 329 | " | " | 0.94 | 658 | " | $Cs^+Cl^-$ | 10.7 | 20 | " | =145 | " |

TABLE II

| Ref | ADDITIVE (nature) | Stb | TT | A | RT P3 | P' | PA | AC9 | DC6 | C4 | VCH |
|---|---|---|---|---|---|---|---|---|---|---|---|
| 1 | $Bu_4N^+Cl^-$ | + | 60.4 | 153 | 77.2 | 0.8 | 3.7 | tr | 4.5 | 13.5 | tr |
| 2 | $MeBu_3N^+Cl^-$ | + | 23.5 | 59 | 76.1 | tr | 2.3 | " | 5.7 | 15.5 | " |
| 3 | $MeOct_4N^+Cl^-$ | + | 70.3 | 163 | 72.8 | 1.3 | 2.9 | 3.2 | 13.0 | 3.3 | 2.7 |
| 4 | $Hex_4N^+Cl^-$ | + | 59.6 | 165 | 84.5 | 1.6 | 1.3 | 1.9 | 3.8 | 5.9 | tr |
| 5 | $Bu_4P^+Cl^-$ | + | 34.8 | 32 | 72.5 | 0.1 | 7.4 | 0.2 | 10.8 | 7 | " |
| 6 | " | + | 29.4 | 41 | 42.5 | 0.3 | 8.4 | 7.2 | 1.9 | 18.9 | 6.8 |
| 7 | " | + | 47.9 | 136 | 86.5 | 1.4 | 1.6 | 0.2 | 3.5 | 5.0 | 0.6 |
| 8 | " | + | 19.1 | 49 | 78.0 | 1.6 | 0.6 | 3.2 | 1.9 | 7.5 | 2.7 |
| 9 | $Hep_4N^+Br^-$ | + | 9.4 | 29 | 82.7 | 1.7 | 5.1 | tr | 4.4 | tr | 6.1 |
| 10 | $Bu_4N^+Cl^-$ | + | 67.5 | 179 | 80.6 | 0.8 | 3.4 | 1.2 | 7.6 | 5.6 | tr |
| 11 | $Bu_4P^+Cl^-$ | + | 54.4 | 113 | 63.0 | 0.5 | 6.6 | 0.5 | 4 | 20.5 | " |
| 12 | " | + | 26.1 | 104 | 62.7 | 0.9 | 0.4 | tr | 1.8 | 31.2 | 0.6 |
| 13 | " | + | 56.6 | 38 | 61.0 | 0.7 | 11.0 | 0.4 | 8.6 | 15.0 | tr |
| 14 | " | + | 53.2 | 135 | 77.0 | 0.8 | 1.6 | 0.9 | 3.3 | 10.2 | 1.4 |
| 15 | $Me_4N^+Cl^-$ | + | 24.7 | 19 | 58.8 | 0.5 | 2.3 | 11.1 | 0.9 | 10.5 | 11.5 |
| 16 | $Bu_4P^+Cl^-$ | + | 29.4 | 52 | 82.2 | 1.8 | 0.3 | 3.2 | 1.3 | 8.4 | 1.6 |
| a | — | 0 | 15.5 | 3 | 5.8 | 0.6 | 1.6 | 0.2 | tr | 89 | 2.9 |
| b | $Cs^+Cl^-$ | 0 | 18 | 25 | 64.4 | " | 0.4 | 19.9 | 0.4 | 9 | 2.2 | that is to say: hydroformylation products of butadiene (pentenals and pentanals) (γ- and δ-valerolactones and -methylbutyrolactone) and chloropentanoic acid: (RT) 7.2% in Example 6, 4.9% in Example 14 and less than 3% in all the other examples.

EXAMPLE 17

Preparation Of 4-Methyl-3-pentenoic Acid From Isoprene

An experiment was carried out with a batch consisting of 278 mmols of isoprene, 278 mmols of water, 0.423 mmols of $PdCl_2$, 21.2 mmols of 1-chloro-but-3-ene and 24.4 mmols of tetrabutylphosphonium chloride ($Bu_4P^+Cl^-$) in the autoclave in accordance with the mode of operation described above.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a unsaturated carboxylic acid, comprising carbonylating a conjugated diene with carbon monoxide in the presence of (i) ater, (ii) a halogenated hydracid, (iii) a palladium catalyst comprising palladium metal or supported palladium metal, a palladium oxide, a complex of palladium, the anion coordinated to the palladium cation comprising a hard or borderline base, or a complex of palladium-O with organic ligands devoid of elements of Group VB of the Periodic Table and (iv) a quaternary onium salt of nitrogen, phosphorus or arsenic, said N, P or As being tetra-coordinated to a carbon atom, the anion comprising a hard or borderline base wherein the temperature and pressure of the carbonylation are greater than 60° C. and 50 bars respectively.

2. The process as defined by claim 1, wherein the quaternary onium salt (iv) comprises a quaternary onium cation having one of the following general formulae (I) to (III):

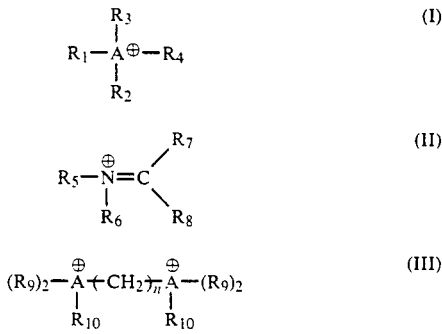

in which A is a nitrogen, phosphorus or arsenic atom; $R_1$, $R_2$, $R_3$ and $R_4$ are identical or different, and each represents a straight or branched chain alkyl radical containing from 1 to 16 carbon atoms, or a substituted alkyl radical containing from 1 to 16 carbon atoms bearing a phenyl, hydroxyl, halogen, nitro, alkoxy or alkoxycarbonyl substituent, said alkoxy substitutent comprising at most 4 carbon atoms; a straight or branched chain alkenyl radical containing from 2 to 12 carbon atoms; or an aryl radical containing from 6 to 10 carbon atoms, or a substituted aryl radical containing from 6 to 10 carbon atoms bearing one or more alkyl substitutents containing from 1 to 4 carbon atoms, alkoxy or alkoxycarbonyl substituents, said alkoxy substituent comprising at most 4 carbon atoms, or a halogen substituent; with the proviso that any two of said radicals $R_1$ to $R_4$ may together form a single straight or branched chain alkylene, alkenylene or alkadienylene radical containing from 3 to 6 carbon atoms; $R_5$, $R_6$, $R_7$ and $R_8$ are identical or different and each represents a straight or branched chain alkyl radical containing from 1 to 4 carbon atoms; with the proviso that the radicals $R_7$ and $R_8$ may together form a single alkylene radical containing from 3 to 6 carbon atoms; and with the further proviso that the radicals $R_6$ and $R_7$, or $R_6$ and $R_8$, may together form a single alkylene, alkenylene or alkadienylene radical containing 4 carbon atoms and, with the nitrogen atom, constitutes a nitrogen-containing heterocyclic radical; $R_9$ represents a straight or branched chain alkyl radical containing from 1 to 4 carbon atoms, or a phenyl radical; $R_{10}$ represents a straight or branched chain alkyl radical containing from 1 to 4 carbon atoms and is identical to or different from $R_9$; or a straight or branched chain alkenyl radical containing from 2 to 12 carbon atoms; and n represents an integer ranging from 1 to 10.

3. The process as defined by claim 2, wherein $R_2$ and $R_{10}$ are alkenyl radicals containing from 4 to 8 carbon atoms.

4. The process as defined by claim 3, wherein $R_2$ and $R_{10}$ are alkenyl radicals derived from the starting material conjugated diene.

5. The process as defined by claim 2, wherein n is an integer of at most 6.

6. The process as defined by claim 2, wherein said quaternary onium cation comprises a tetramethylammonium, tetrabutylammonium, tetrahexylammonium, tetraheptylammonium, methyltributylammonium, methyltrioctylammonium or tetrabutylphosphonium cation.

7. The process as defined by claim 1, wherein the anion of said onium salt comprises $PO_4^{3-}$, $HPO_4^{2-}$, $H_2PO_4^-$, $CH_3SO_3^-$, $Ph-SO_3^-$, $NO_3^-$, $SO_4^{2-}$, $PF_6^-$, $Cl^-$ or $Br^-$, wherein Ph is phenyl.

8. The process as defined by claim 1, wherein the palladium catalyst anion coordinated to the palladium cation is a carboxylate, $SO_4^{2-}$, $NO_3^-$, acetylacetonate, chloride or bromide anion.

9. The process as defined by claim 1, wherein the molar ratio of water/conjugated diene ranges from 0.1:1 to 5:1; the molar ratio of conjugated diene/palladium ranges from 100:1 to 2,500:1; the molar ratio of onium cation/palladium is at least 15:1 and the molar ratio of halogenated hydracid/palladium is at least 5:1.

10. The process as defined by claim 9, wherein the molar ratio of water/conjugated diene ranges from 0.5:1 to 2:1; the molar ratio of conjugated diene/palladium ranges from 200:1 to 1,500:1; the molar ratio of onium cation/palladium ranges from 20:1 to 300:1; and the molar ratio of halogenated hydracid/palladium ranges from 10:1 to 150:1.

11. The process as defined by claim 10, wherein the molar ratio of halogenated hydracid/palladium ranges from 20:1 to 100:1.

12. A process for the preparation of 3-pentenoic acid, comprising carbonylating butadiene with carbon monoxide in the presence of (i) water, (ii) hydrochloric acid, (iii) a palladium catalyst comprising palladium-II chloride or bis[π-allyl-palladium-II chloride], and (iv) a quaternary onium salt of nitrogen, phosphorus or arsenic, said N, P or As being tetracoordinated to a carbon atom, the anion of which comprising a hard or borderline base, and wherein the molar ratio of water/butadiene ranges from 0.5:1 to 2:2, the molar ratio of onium cation/palladium ranges from 20:1 to 300:1 and the molar ratio of hydrochloric acid/palladium ranges from 10:1 to 150:1 wherein said carbonylation is carried out at a reaction temperature ranging from 60° to 170° C. and under a carbon monoxide pressure ranging from 50 to 500 bars.

13. The process as defined by claim 12 wherein carbonylation is carried out at a reaction temperature ranging from 90° to 140° C. and under a carbon monoxide pressure ranging from 80 to 300 bars.

14. A process for the preparation of an unsaturated carboxylic acid, comprising carbonylating a conjugated diene with carbon monoxide in the presence of (i) water, (ii) a halogenated hydracid, (iii) a palladium catalyst comprising palladium metal or supported palladium metal, a palladium oxide, a salt of palladium, the anion coordinated to the palladium cation comprising a hard or borderline base and or a complex of palladium-O with organic ligands devoid of elements of Group VB of the Periodic Table and (iv) a quaternary onium salt of nitrogen, phosphorus or arsenic, said N, P or As being tetra-coordinated to a carbon atom, the anion comprising a hard or borderline base wherein said carbonylation is carried out à reaction temperature greater than 60° C. and under an overall pressure of greater than 50 bars.

15. The process as defined by claim 14, wherein the quaternary onium salt (iv) comprises a quaternary onium cation having one of the following general formulae (I) to (III):

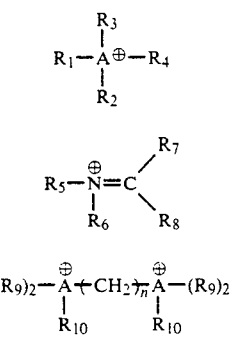

in which A is a nitrogen, phosphorus or arsdenic atom; $R_1$, $R_2$, $R_3$ and $R_4$ are identical or different, and each represents a straight or branched chain alkyl radical containing from 1 to 16 carbon atoms, or a substituted alkyl radical containing from 1 to 16 carbon atoms bearing a phenyl, hydroxyl, halogen, nitro, alkoxy or alkoxycarbonyl substituent, said alkoxy substituent comprising at most 4 carbon atoms; a straight or branched chain alkenyl radical containing from 2 to 12 carbon atoms; or an aryl radical containing from 6 to 10 carbon atoms, or a substituted aryl radical containing from 6 to 10 carbon atoms bearing one or more alkyl substituents containing from 1 to 4 carbon atoms, alkoxy or alkoxycarbonyl substituents, said alkoxy substituent comprising at most 4 carbon atoms, or a halogen substituent; with the proviso that any two of said radicals $R_1$ to $R_4$ may together form a single straight or branched chain alkylene, aleknylene or alkadienylene radical containing from 3 to 6 carbon atoms; $R_5$, $R_6$, $R_7$ and $R_8$ are identical or different and each represents a straight or branched chain alkyl radical containing from 1 to 4 carbon atoms; with the proviso that the radicals $R_7$ and $R_8$ may together form a single alkylene radical containing from 3 to 6 carbon atoms; and with the further proviso that the radicals $R_6$ and $R_7$, or $R_6$ and $R_8$, may together form a single alkylene, alkenylene or alkadienylene radical containing 4 carbon atoms and, with the nitrogen atom, constitutes a nitrogen-containing heterocyclic radical; $R_9$ represents a straight or branched chain alkyl radical containing from 1 to 4 carbon atoms, or a phenyl radical; $R_{10}$ represents a straight or branched chain alkyl radical containing from 1 to 4 carbon atoms and is identical to or different from $R_9$; or a straight or branched chain alkenyl radical containing from 2 to 12 carbon atoms; and n represents an integer ranging from 1 to 10.

16. The process as defined by claim 15, wherein $R_2$ and $R_{10}$ are alkenyl radicals containing from 4 to 8 carbon atoms.

17. The process as defined by claim 15, wherein $R_2$ and $R_{10}$ are alkenyl radicals derived from the starting material conjugated diene.

18. The process as defined by claim 15, wherein n is an integer of at most 6.

19. The process as defined by claim 15, wherein said quaternary onium cation comprises a tetramethylammonium, tetrabutylammonium, tetrahexylammonium, tetraheptylammonium, methyltributylammonium, methyltrioctylammonium or tetrabutylphosphonium cation.

20. The process as defined by claim 14, wherein the anion of said onium salt comprises $PO_4^{3-}$, $HPO_4^{2-}$, $H_2PO_4^-$, $CH_3SO_3^-$, $Ph\text{-}SO_3^-$, $NO_3^-$, $SO_4^{2-}$, $PF_6^-$, $Cl^-$ or $Br^-$, wherein Ph is phenyl.

21. The process as defined by claim 14, wherein the palladium catalyst comprises a palladium salt in which the anion coordinated to the palladium cation is a carboxylate, $SO_4^{2-}$, $NO_3^-$, acetylacetonate, chloride or bromide anion.

22. The process as defined by claim 14, wherein the molar ratio of water/conjugated diene ranges from 0.1:1 to 5:1; the molar ratio of conjugated diene/palladium ranges from 100:1 to 2,500:1; the molar ratio of onium cation/palladium is at least 15:1 and the molar ratio of halogenated hydracid/palladium is at least 5:1.

23. The process as defined by claim 22, wherein the molar ratio of water/conjugated diene ranges from 0.5:1 to 2:1; the molar ratio of conjugated diene/palladium ranges from 200:1 to 1,500:1; the molar ratio of onium cation/palladium ranges from 20:1 to 300:1; and the molar ratio of halogenated hydracid/palladium ranges from 10:1 to 150:1.

24. The process as defined by claim 23, wherein the molar ratio of halogenated hydracid/palladium ranges from 20:1 to 100:1.

* * * * *